United States Patent
Vadillo et al.

(10) Patent No.: US 12,194,179 B2
(45) Date of Patent: Jan. 14, 2025

(54) OBJECT SANITIZER USING OZONE AND IONIC AIR MOVER

(71) Applicant: Ventiva, Inc., Pleasanton, CA (US)

(72) Inventors: Rudy Vadillo, Gilroy, CA (US); Himanshu Pokharna, Saratoga, CA (US); Gary Alfred Oliverio, San Jose, CA (US); Jeffrey S. Nespor, Pleasanton, CA (US)

(73) Assignee: Ventiva, Inc., Pleasanton, CA (US)

( * ) Notice: Subject to any disclaimer, the term of this patent is extended or adjusted under 35 U.S.C. 154(b) by 587 days.

(21) Appl. No.: 17/562,830

(22) Filed: Dec. 27, 2021

(65) Prior Publication Data

US 2022/0202976 A1    Jun. 30, 2022

Related U.S. Application Data

(60) Provisional application No. 63/131,425, filed on Dec. 29, 2020.

(51) Int. Cl.
*A61L 2/20*    (2006.01)
*A61L 2/10*    (2006.01)
*A61L 2/24*    (2006.01)

(52) U.S. Cl.
CPC ............ *A61L 2/202* (2013.01); *A61L 2/10* (2013.01); *A61L 2/24* (2013.01); *A61L 2202/11* (2013.01); *A61L 2202/121* (2013.01); *A61L 2202/122* (2013.01); *A61L 2202/14* (2013.01); *A61L 2202/15* (2013.01); *A61L 2202/20* (2013.01)

(58) Field of Classification Search
None
See application file for complete search history.

(56) References Cited

U.S. PATENT DOCUMENTS

2013/0019503 A1 * 1/2013 Vogt ................ A43B 7/005
                                                    320/108

FOREIGN PATENT DOCUMENTS

WO    WO-2016106344 A1 *  6/2016  ............... A61L 2/10
WO    WO 2020/223300 A1    11/2020

* cited by examiner

*Primary Examiner* — Natasha E Young
(74) *Attorney, Agent, or Firm* — Fenwick & West LLP (57) ABSTRACT

A sanitizing device includes an enclosed chamber, an ionic air mover and a closed recirculation path. The chamber is designed to contain the object to be sanitized. For example, if the object is a mobile phone (or other portable electronics or small objects), the chamber may have the same approximate shape as the mobile phone. The chamber may contain a lid that is opened to allow insertion of the mobile phone into the chamber and then closed with a good seal to create an enclosed chamber with low leakage. The ionic air mover performs two functions. It creates an air flow through the use of corona discharge. It also ionizes oxygen to create ozone that will be used to sanitize the object of interest.

20 Claims, 8 Drawing Sheets

OBJECT SANITIZER USING OZONE AND IONIC AIR MOVER

CROSS-REFERENCE TO RELATED APPLICATION(S)

This application claims priority under 35 U.S.C. § 119(e) to U.S. Provisional Patent Application Ser. No. 63/131,425, "Object Sanitizer Using Ozone and Ionic Air Mover," filed Dec. 29, 2020. The subject matter of all of the foregoing is incorporated herein by reference in its entirety.

BACKGROUND

1. Technical Field

This disclosure relates generally to sanitizing objects by using concentrated ozone.

2. Description of Related Art

The recent coronavirus pandemic has demonstrated the importance of vigilant sanitization in order to reduce the spread of disease. Virus, bacteria and other pathogens may be spread through contact with contaminated surfaces. An infected person may leave pathogens on a surface by coughing, sneezing, touching or other means. Those pathogens may persist for some period of time. Another person may then pick up the pathogens by contacting the contaminated surface.

This cycle may be reduced or broken by sanitizing the surface, reducing or eliminating the pathogen population on the surface. Disinfecting wipes, ultraviolet light and other means may be used to regularly sanitize objects. However, not all methods are equally effective, and some methods may not be appropriate for some objects. In addition, convenience, low power, low cost, and portability are desirable characteristics for any sanitization approach.

Thus, there is a need for better and different approaches to sanitization.

BRIEF DESCRIPTION OF THE DRAWINGS

Embodiments of the disclosure have other advantages and features which will be more readily apparent from the following detailed description and the appended claims, when taken in conjunction with the examples in the accompanying drawings, in which:

DETAILED DESCRIPTION OF THE PREFERRED EMBODIMENTS

The figures and the following description relate to preferred embodiments by way of illustration only. It should be noted that from the following discussion, alternative embodiments of the structures and methods disclosed herein will be readily recognized as viable alternatives that may be employed without departing from the principles of what is claimed.

Figure 1:
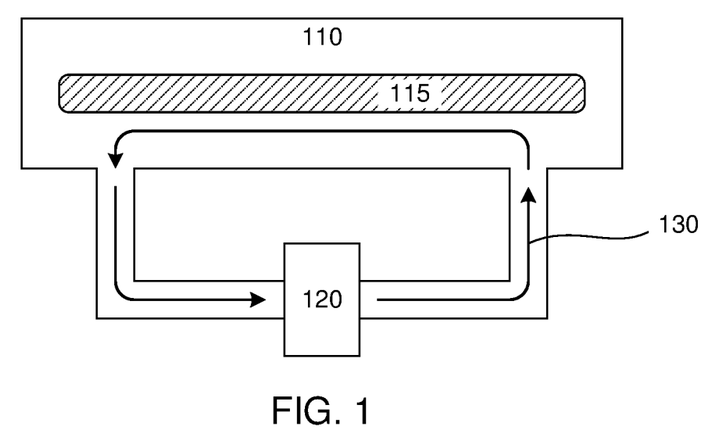
FIG. 1 is a simplified diagram of a sanitizing device according to the present disclosure.

FIG. 1 is a simplified diagram of a sanitizing device according to the present disclosure. The device includes an enclosed chamber 110, an ionic air mover 120 and a closed recirculation path 130 as indicated by the arrows. The chamber 110 is designed to contain the object 115 to be sanitized. For example, if the object 115 is a mobile phone (or other portable electronics or small objects), the chamber 110 may have the same approximate shape as the mobile phone. The chamber 110 may contain a lid that is opened to allow insertion of the mobile phone into the chamber and then closed with a good seal to create an enclosed chamber 110 with low leakage.

The ionic air mover 120 performs two functions. It creates an air flow, and it also ionizes oxygen to create ozone that will be used for the sanitization. The ionic air mover 120 produces an air flow through the use of corona discharge. The ionic air mover includes an emitter and a collector. The emitter includes sharper (corona) electrodes and the collector includes blunter (neutralizing) electrodes. When an electric field is applied across these electrodes, this causes a partial breakdown of the gas between the emitter and collector, referred to as a corona discharge. The corona discharge occurs near the emitter and produces ions that are attracted to the neutralizing collector. En route, the ions collide with neutral air molecules creating a pressure head resulting in an air flow. Further examples and descriptions of ionic air movers 120 are included in PCT application PCT/US2020030397 "Ionic Wind Generator" and U.S. provisional applications 62/840,332 and 62/882,928, which are all incorporated herein by reference.

Operation of the ionic air mover also ionizes the air. Ionizing oxygen in the air results in the creation of ozone ($O_3$). For many applications, the creation of ozone may be an undesirable byproduct of operating the ionic air mover. This application, however, takes advantage of the ozone production. The ozone will be further concentrated and used to sanitize the object of interest. One advantage of the sanitizing devices described herein is that a single component—the ionic air mover—both creates an air flow and also ionizes a part of the oxygen into ozone. Furthermore, the ionic air mover is a solid state component, so there are no moving parts. Compared to a device which has one component to create ozone (such as an electrode configuration with a corona discharge) and a separate component to create air flow (such as a mechanical fan), the use of a single component to perform both functions allows the entire volume of circulating air to pass through the coronal discharge of the ionic air mover in each circulation round, very quickly achieving and efficiently maintaining ozone concentration sufficient for sanitization, while significantly reducing the overall size, the complexity of integrating and controlling separate components, the cost, and the power consumed.

If the ozone produced by the ionic air mover 120 were simply blown across the surface of the object 115 in an open air environment, it typically would not be concentrated enough to sanitize the object. Even if sufficient ozone were produced to sanitize objects in an open air environment, that approach would have an undesirable adverse impact on the ambient air quality near the device due to lung irritation caused by inhalation of ozone in high concentrations. To remedy this problem, a closed recirculation path 130 concentrates the ozone. The recirculation path 130 is closed, meaning that the air (and ozone) recirculates within a closed volume. Air within the recirculation path 130 flows from the ionic air mover 120 through the enclosed chamber 110 and back to the ionic air mover. There are no significant leakage paths to/from this closed volume. In a preferred embodiment, during each circulation the entire volume of moving air passess through the ionic air mover. As a result, the concentration of ozone rapidly builds up over time and is efficiently maintained. The recirculation coupled with ozone production from the ionic air mover 120 creates concentrated ozone in the enclosed chamber 110 sufficient for sanitization. The object 115 is positioned in the recirculation path, is exposed to the concentrated ozone and is thereby sanitized.

Figure 2:
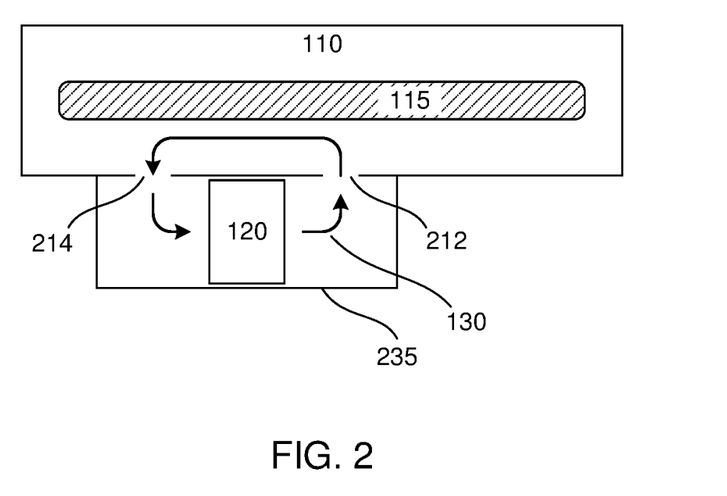
FIG. 2 is a simplified diagram of another sanitizing device according to the present disclosure.

FIG. 2 is a simplified diagram of another sanitizing device according to the present disclosure. In this example, the ionic air mover 120 is contained in a separate enclosed chamber 235, which will be referred to as the auxiliary chamber. The two chambers 110, 235 are connected by ports 212, 214 between the chambers: an inlet port 212 to the sanitizing chamber 110, and an outlet port 214 from sanitizing chamber 110. The recirculation path 130 is from the ionic air mover 120 through the inlet port 212 to the sanitizing chamber 110, and through outlet port 214 back to the ionic air mover. Note that not all of the object 115 is in the direct recirculation path 130. In FIG. 2, only a portion of the bottom surface of the object 115 is directly in the recirculation path. However, the rest of the object 115 is still exposed to sufficient concentration of ozone as a result of diffusion or other transport mechanisms. In this example, the ionic air mover 120 itself spans the entire width of the auxiliary chamber 235, thus forcing air to flow through the recirculation path 130 rather than through some other "shortcut" path from one side of the ionic air mover to the other.

Figure 3:
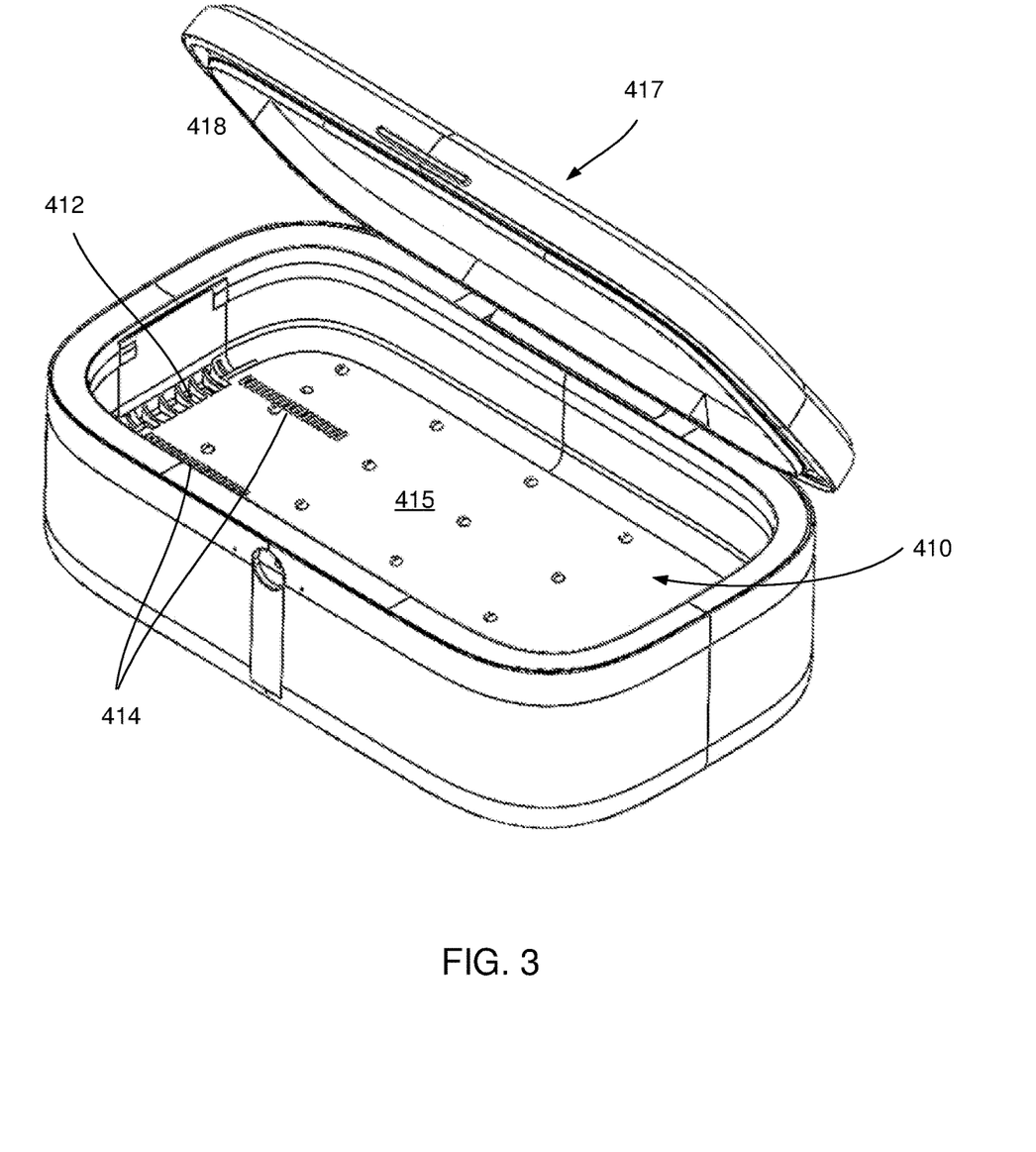
FIG. 3 is a perspective view of a device for sanitizing a cell phone.

FIGS. 3 and 4 are different views of a specific design for sanitizing a cell phone. This design is an implementation of the approach shown in FIG. 2, where a separate chamber encloses the ionic air mover.

FIG. 3 is a rendering of a perspective view of the device with the lid 417 open to expose the sanitizing chamber 410, to allow insertion of the cell phone. The seal 418 between the lid 417 and the rest of the chamber 410 reduces ozone leakage from the enclosed chamber to acceptable levels, thus preserving the required concentration of ozone within the sanitizing chamber 410. In this example, the seal 418 has a tongue and groove construction, although compliant gaskets or other types of seals may also be used. In FIG. 3, the ionic air mover lies below the bottom surface 415 of the sanitizing chamber 410. The sanitizing chamber 410 is constructed from ozone-compatible materials, such as ABS or polycarbonate. Slits 412 and 414 are the inlet port and outlet port, respectively, between the ionic air mover and the sanitizing chamber 410. Air flows through inlet slits 412 into the sanitizing chamber 410 and back to the ionic air mover via the outlet slits 414. The floor 415 of the sanitizing chamber also contains raised dimples that support the cell phone away from the bottom surface, so that air can flow between the cell phone and the floor of the sanitizing chamber 410. Other types of standoff features may also be used.

Figure 4A:
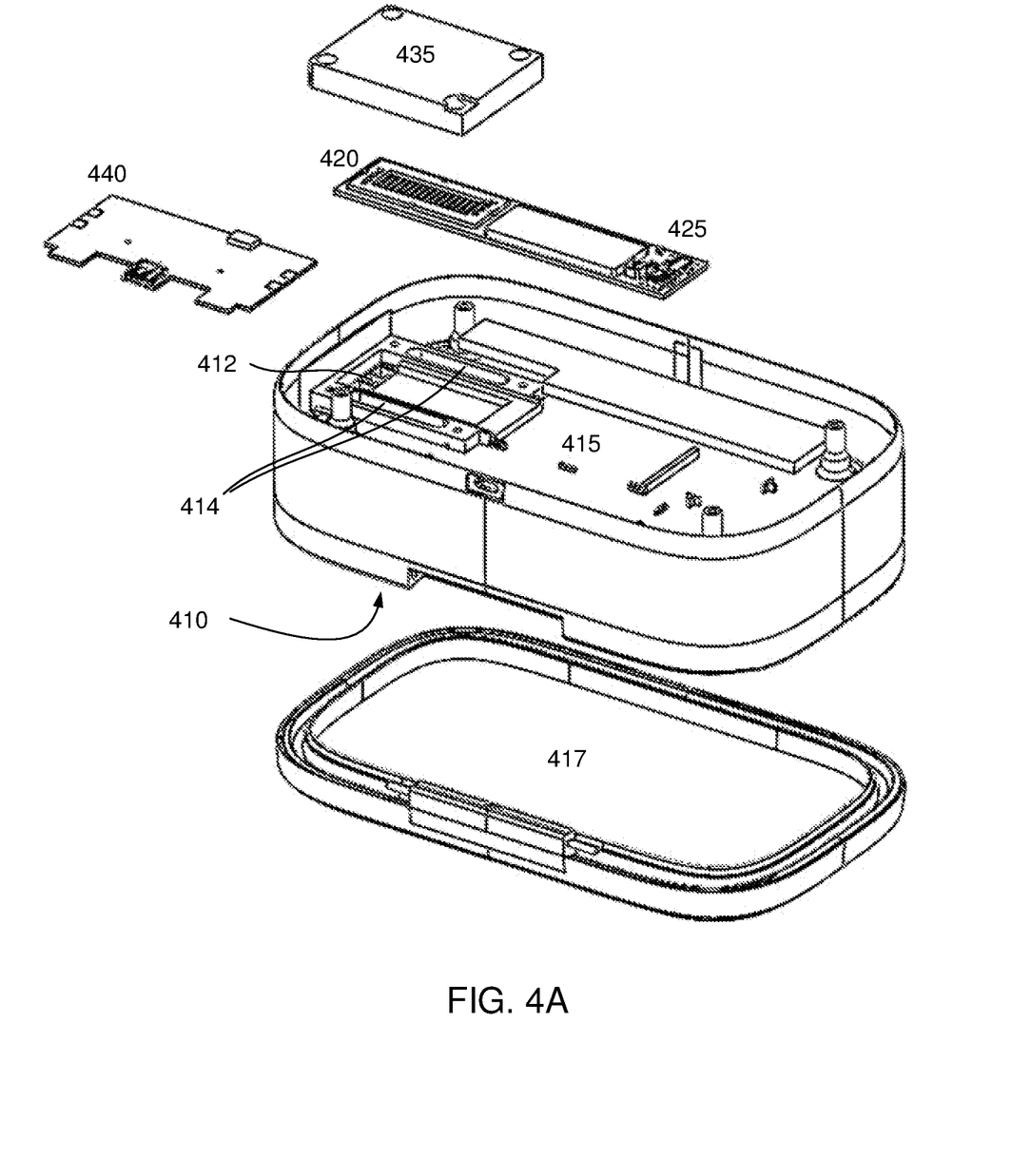
FIG. 4A is an exploded view of the sanitizing device.

FIG. 4A is a rendering of an exploded view of the sanitizing device. The device is turned upside down relative to FIG. 3 and the bottom assembly is exploded to make the different components visible. The bottom assembly includes an enclosed chamber 435 that contains the ionic air mover 420. The ionic air mover 420 is mounted on a printed circuit board (PCB) 425, which is partially inside the auxiliary chamber 435 and partially outside the chamber. Other electronics are also visible. When assembled, the ozone is largely contained within the auxiliary chamber 435, so the electronics outside the chamber are not exposed to ozone. This view also shows the inlet and outlet ports 412 and 414 and the bottom side of the floor 415 of the sanitizing chamber. The lid 417 is also visible, but the main sanitizing chamber 410 is not visible from this angle. The device may also contain other components, for example additional printed circuit board 440. In some embodiments, PCB 440 contains electronics that control wireless charging functionality.

Figure 4B:
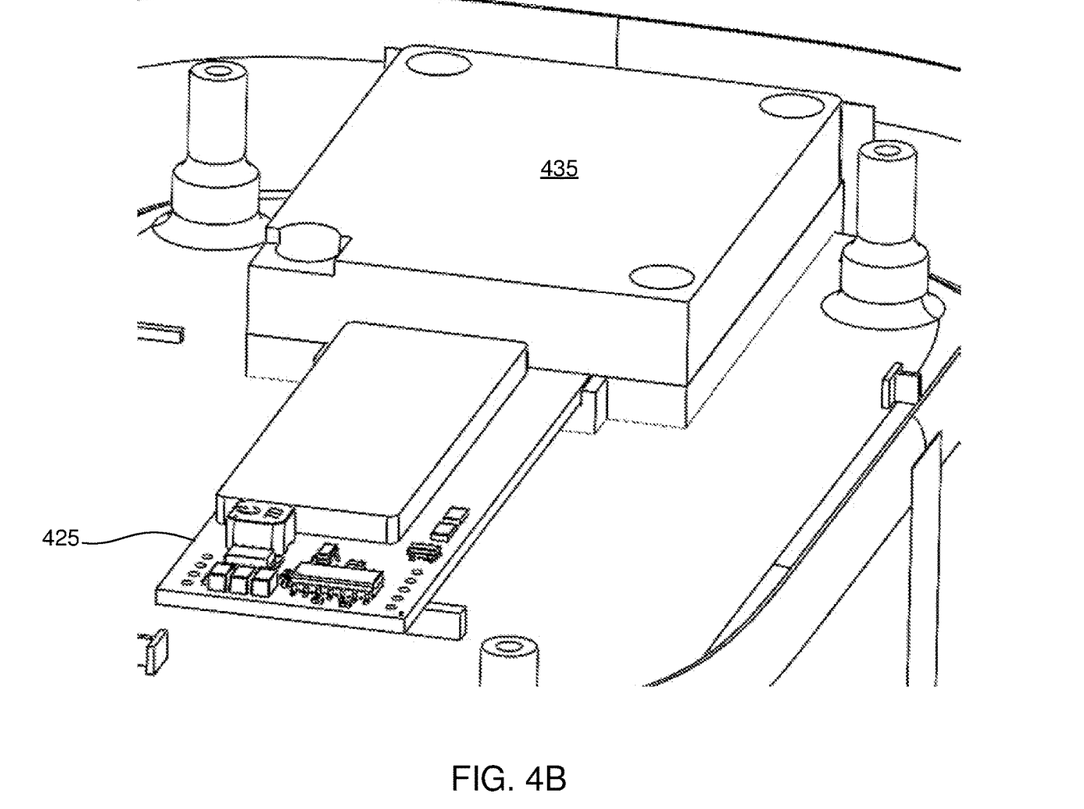
FIG. 4B is a close-up view of a bottom assembly of the sanitizing device, showing a printed circuit board entering an auxiliary chamber for the ionic air mover.
Figure 4C:
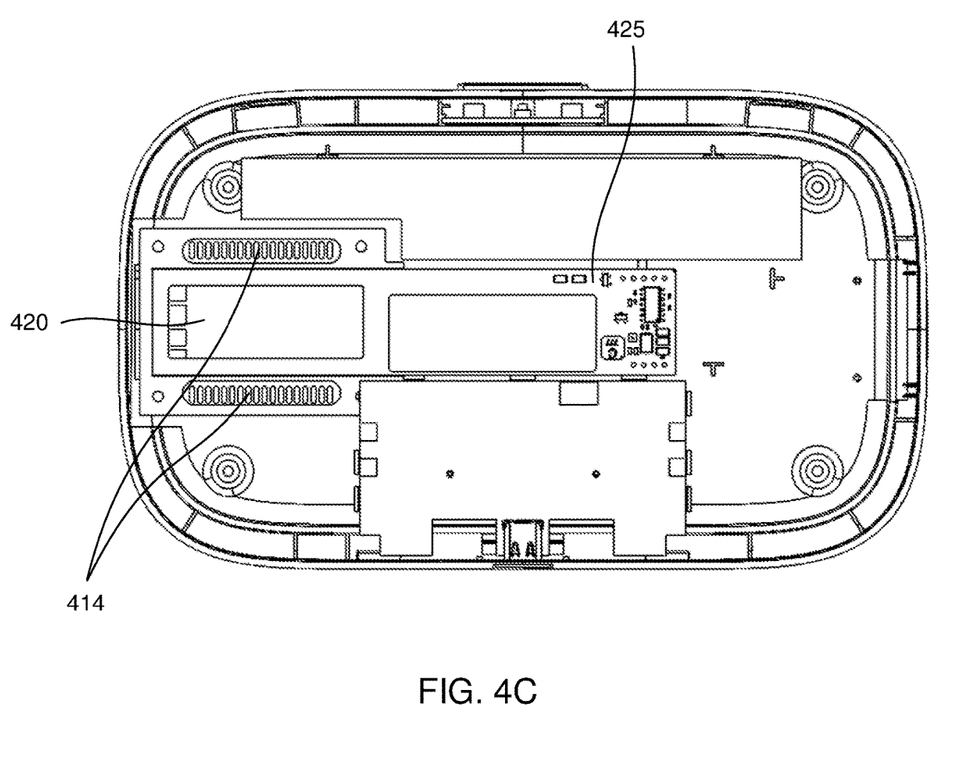
FIG. 4C is a view of a bottom assembly of the sanitizing device, with the auxiliary chamber removed.

FIG. 4B is a close-up view showing the printed circuit board 425 and the auxiliary chamber 435 assembled in place. FIG. 4C is a view of the bottom assembly of the sanitizing device, with the auxiliary chamber 435 removed, so that the ionic air mover 420 is visible. The outlet slits 414 are also visible. The inlet slits are hidden by the printed circuit board 425.

Figure 4D:
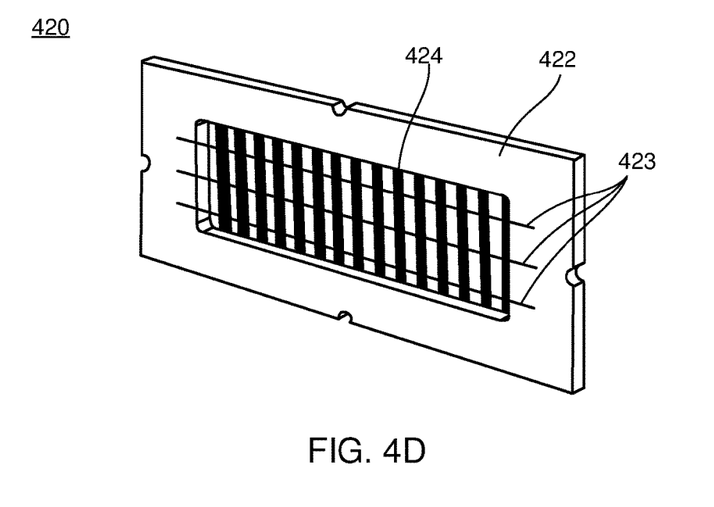
FIG. 4D is a perspective view of the ionic air mover.

FIG. 4D is a perspective view of the ionic air mover 420. The ionic air mover 420 includes a substrate 422 with two sides and a hole through the substrate. Here, the substrate is printed circuit board. The emitter 423 is implemented as a set of parallel wires on one side of the substrate]. The collector 424 is implemented as a set of pins or some other columnar structure perpendicular to the emitter wires on the other side of the substrate. A voltage applied to the emitter 423 ionizes air, and the ionized air (including ozone) is drawn to the collector 424 to produce the air flow. This design is simple to make and inexpensive. It also leverages the existing infrastructure in place to process PCBs: surface mounting, etc. It also works on relatively lower voltage compared to other designs such as a point and ring, or point and plates, or a wire and parallel plates. This is just one example design for an ionic air mover. Other designs may also be used.

When in operation, the ionic air mover 420 applies high voltage between the emitter 423 and collector 424. In the configuration of FIG. 4, the end user has access to the sanitizing chamber but not to the bottom assembly. The ionic air mover 420 is not physically accessible to the end user, so they cannot be exposed to the high voltage.

Figure 5:
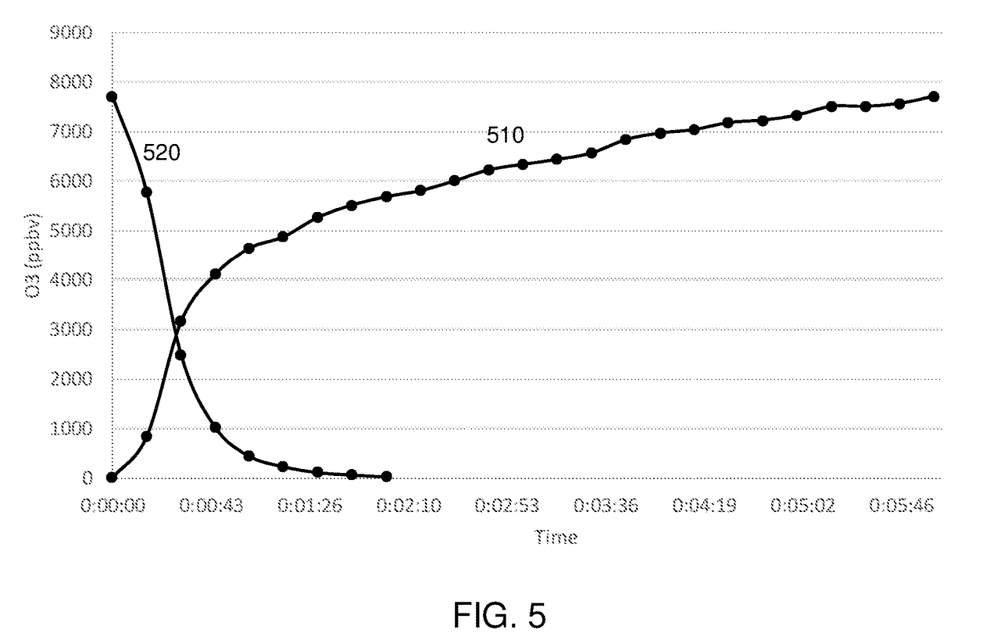
FIG. 5 is a graph showing ramp up and ramp down of ozone concentration for a sanitizing device.

As described above, the closed sanitizing chamber 410 and closed recirculation path result in the buildup of ozone concentration sufficient to sanitize the object 115. FIG. 5 is a graph showing ramp up and ramp down of ozone concentration for the sanitizing device of FIGS. 3-4. Curve 510 shows ramp up of ozone concentration, applying 0.8 watts of power where the sanitizing chamber contains a phone. There is a tradeoff between ozone concentration and time required to reach a certain level of sanitization. At an ozone concentration of 4000 ppb (parts per billion, at a standard ambient atmospheric pressure and temperature), >99% sanitization of common bacteria can be accomplished in 240 seconds. In FIG. 5, the ramp up to 4000 ppb takes approximately 45 seconds. If sanitization is run at other concentrations—2000 ppb or lower, or 7000-8000 ppb or higher—the ramp up time and sanitization time will vary. In some embodiments, the ozone concentration in the sanitizing chamber reaches at least 2000 ppb in not more than 120 seconds. Power consumption preferably is less than 2 watts per liter of volume in the sanitizing chamber.

Once the sanitizing is completed, the ozone concentration is reduced before the sanitizing chamber is opened. Otherwise, the end user or other objects may be exposed to high concentrations of ozone. Ozone is an unstable gas and over time it converts back into oxygen. Curve 520 in FIG. 5 shows ramp down of ozone concentration, after sanitization is completed. In this example, concentration falls from 8000 ppb to under 1000 ppb in approximately 45 seconds.

In some embodiments, the ozone may be actively dissipated or purged. For example, at the end of the sanitization cycle, a vent or other air path may be opened for the ozoneated air. A non-ozone producing conventional fan may be used to actively exhaust the ozone-laden air. The ozone may also pass through a catalyst that breaks down the ozone before it is exhausted to ambient air. The catalyst could be an open honeycomb lattice with sufficient surface area to allow the catalytic coating the ability to reduce ozone to acceptable levels to maintain ambient air quality within regulatory limits (typically, an 8-hour average increase in ambient room air ozone no greater than 70 ppb under California and U.S. air quality standards).

Figure 6:
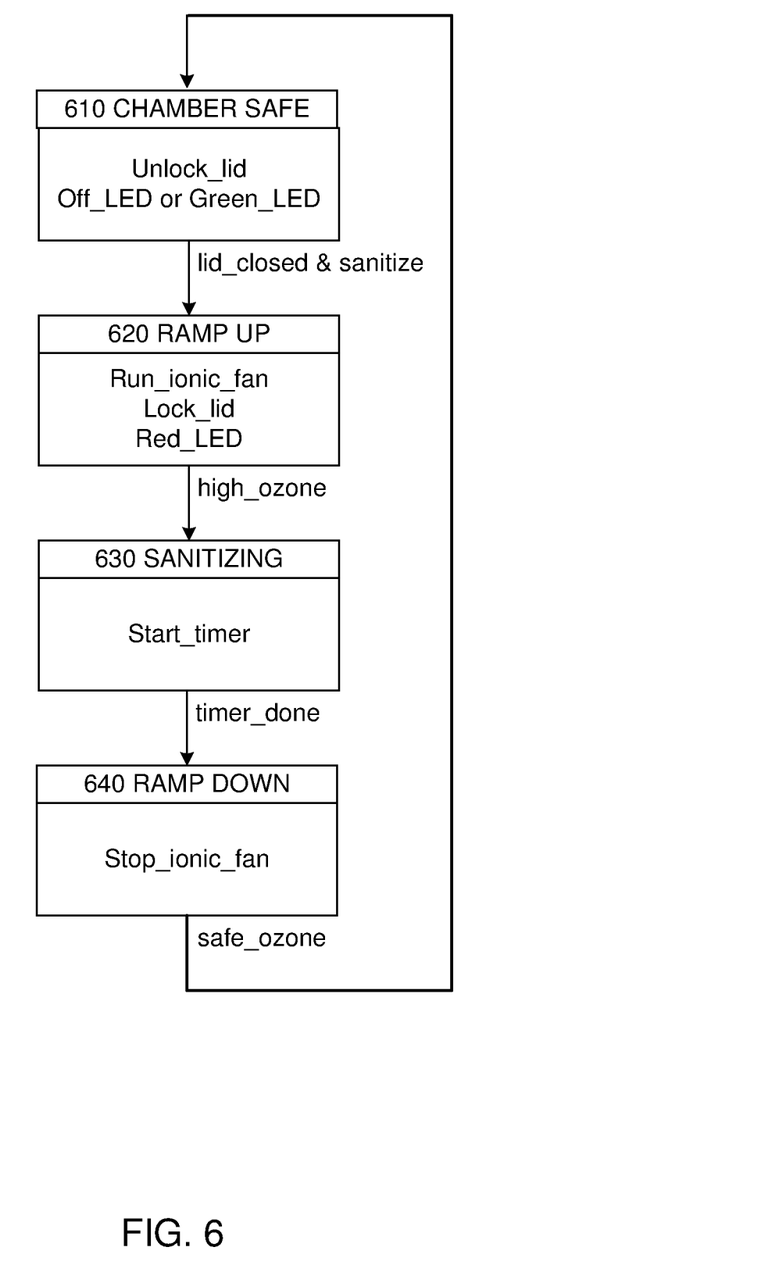
FIG. 6 is a state diagram for operation of the sanitizing device.

FIG. 6 is a state diagram for operation of the sanitizing device. The states are as follows:

CHAMBER SAFE (610). The sanitizing chamber is open or is safe to open to allow insertion or retrieval of the object. Ozone concentration is below an acceptable limit.

RAMP UP (620). Ozone concentration in the sanitizing chamber is ramping up.

SANITIZING (630). Ozone concentration in the sanitizing chamber is sufficient for sanitization.

RAMP DOWN (640). Ozone concentration in the sanitizing chamber is ramping down.

The chamber may not be open when it contains significant amounts of ozone. Thus, the sanitizing device may be operated as follows. In this example, the device contains an ozone concentration sensor and LED(s) are used as indicators of the state.

1. Assume that the device begins in the CHAMBER SAFE state with an open lid. The indicator LED is off.
2. Place the object of interest inside the sanitizing chamber and close the lid. Press a button to start the sanitization cycle. When the device detects that the lid is closed and the start button has been pressed, it transitions to the RAMP UP state. The ionic air mover is started. The lid is locked. A red LED is turned on to indicate active sanitization.
3. A sensor measures the ozone concentration. When the concentration reaches a predetermined threshold, say 2000 ppb, the state transitions to the SANITIZING state. If there is no sensor, the ramping up could be time-based instead. The device remains in this state for a predetermined amount of time sufficient to sanitize the object.
4. After the timer times out, the device transitions to the RAMP DOWN state. In this state, the ionic air mover is turned off and the ozone concentration drops over time.
5. The device remains in the RAMP DOWN state until ozone concentration drops to a safe level (say 1000 ppb), at which time it transitions to the CHAMBER SAFE state. The LED remains red until the device reaches the CHAMBER SAFE state. The lid is unlocked. The LED turns green to indicate that the sanitization cycle is completed. Other indicators may also be used, for example an audio signal or messaging to an app. It is safe to open the chamber and retrieve the sanitized payload. From the CHAMBER SAFE state, the user may open the lid.

If there is no lock on the lid, a safety interlock may turn off the ionic air mover if the lid is opened prematurely. Early termination can be reflected via LED activity (e.g. blinking red for a period of time). Immediately closing the lid does not restart ozone generation.

Other safety interlocks may also be used. For example, a safety interlock may prevent operation of the ionic air mover when the sanitizing chamber is open or when there is no object in the chamber. A safety interlock may also prevent opening of the sanitizing chamber until the concentration of ozone in the chamber drops below an acceptable level or until the ionic air mover has been turned off for a certain amount of time.

Figure 7:
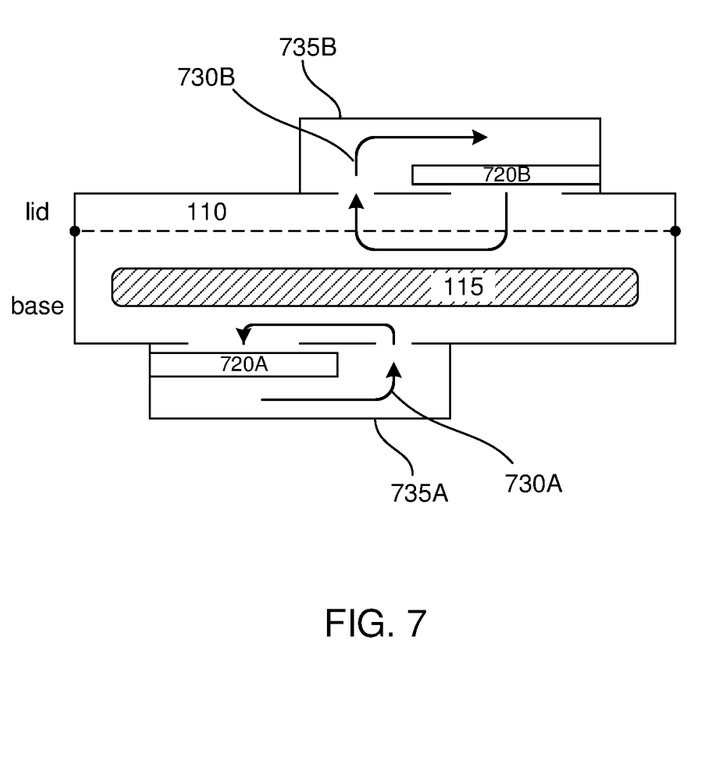
FIG. 7 is a simplified diagram of yet another sanitizing device according to the present disclosure.

More sophisticated control may also be used. For example, the air flow and/or the power or voltage to the ionic air mover may be adjusted based on the measured ozone concentration in the sanitizing chamber. The device may also have multiple ionic air movers. FIG. 7 shows an example in which there is an ionic air mover 720A in the base of the device and another ionic air mover 720B in the lid. Each ionic air mover 720A,B is enclosed in a separate chamber 735A,B, with a separate closed recirculation path 730A,B. In some cases, different ionic air movers may be turned on based on the payload or based on the ozone concentration sensor, providing multi-stage sanitization.

Devices may combine ozone sanitization with other functions. For example, the device may also include a wireless charger for charging the object. Charging may begin when the electronics is placed in the chamber, regardless of the lid position or whether sanitization is also taking place. If the lid is closed and the button is pushed, sanitization proceeds as previously described. Charging may continue during and after the sanitization cycle.

As a final example, ozone-based sanitization may be combined with other types of sanitization. For example, the device may also include an ultraviolet source that creates ultraviolet radiation to sanitize the object in the enclosed chamber in conjunction with or as an alternative to the concentrated ozone.

Although the detailed description contains many specifics, these should not be construed as limiting the scope of the invention but merely as illustrating different examples. It should be appreciated that the scope of the disclosure includes other embodiments not discussed in detail above. Various other modifications, changes and variations which will be apparent to those skilled in the art may be made in the arrangement, operation and details of the method and apparatus disclosed herein without departing from the spirit and scope as defined in the appended claims. Therefore, the scope of the invention should be determined by the appended claims and their legal equivalents.

What is claimed is:

1. A device for sanitizing the surface of an object, the device comprising:
   an enclosed chamber configured to contain the object to be sanitized;
   an ionic air mover that creates an air flow and that also ionizes oxygen, thereby creating ozone in the air flow; and
   a closed recirculation path from the ionic air mover through the enclosed chamber and back to the ionic air mover, wherein the recirculation creates concentrated ozone in the enclosed chamber sufficient for sanitization, and a surface of the object is positioned in the recirculation path and thereby exposed to the concentrated ozone.

2. The device of claim 1 wherein the ionic air mover without the closed recirculation path does not create ozone in a concentration sufficient for sanitization.

3. The device of claim 1 wherein the ionic air mover is not physically accessible to an end user from the enclosed chamber.

4. The device of claim 3 further comprising:
a second enclosed chamber that contains the ionic air mover, wherein the closed recirculation path comprises an inlet port for air flow from the ionic air mover to the enclosed chamber holding the object, and an outlet port for return air flow from the enclosed chamber holding the object to the ionic air mover.

5. The device of claim 1 wherein the ionic air mover comprises:
a substrate with two sides and a hole in the substrate;
a collector on one side of the substrate and an emitter on the other side of the substrate;
wherein a voltage applied to the emitter ionizes air that is drawn to the collector to produce the air flow, and the closed recirculation path is from the collector through the enclosed chamber and back to the emitter.

6. The device of claim 5 wherein the substrate also prevents air flow from the collector back to the emitter by paths other than the closed recirculation path.

7. The device of claim 5 wherein the substrate comprises a printed circuit board.

8. The device of claim 7 further comprising:
a second enclosed chamber that contains a portion of the printed circuit board with the ionic air mover, but wherein a portion of the printed circuit board containing electronics lies outside both enclosed chambers and the electronics are not exposed to the concentrated ozone.

9. The device of claim 1 wherein the ozone in the enclosed chamber reaches a concentration of at least 2 ppm in not more than 120 seconds.

10. The device of claim 1 wherein the closed recirculation path does not include all of the enclosed chamber, but the ozone reaches a concentration sufficient for sanitization throughout all of the enclosed chamber.

11. The device of claim 1 wherein the device consumes less than 2 watts power per liter of volume in the enclosed chamber.

12. The device of claim 1 further comprising:
a second ionic air mover with a second closed recirculation path through the enclosed chamber.

13. The device of claim 1 further comprising:
a sensor that measures the concentration of ozone in the enclosed chamber; and
a controller that adjusts the air flow based on the measured concentration of ozone in the enclosed chamber and/or adjusts a power to the ionic air mover based on the measured concentration of ozone in the enclosed chamber.

14. The device of claim 1 further comprising:
a safety interlock that prevents operation of the ionic air mover when the enclosed chamber is open and/or that prevents opening of the enclosed chamber until the concentration of ozone in the enclosed chamber drops below an acceptable level.

15. The device of claim 1 further comprising:
an indicator that is observable by an end user and that indicates a state of operation of the device.

16. The device of claim 15 wherein the indicator indicates at least one of the following: (a) that the device is in a state of building the concentration of ozone; (b) that the device is in a state of sanitizing the object with sufficient concentration of ozone; (c) that the device is in a state of completed sanitizing the object but where the concentration of ozone in the enclosed chamber is not low enough to allow opening of the chamber; or (d) that the device is in a state where the concentration of ozone in the enclosed chamber is low enough to allow opening of the chamber.

17. The device of claim 1 further comprising:
an ultraviolet source that creates ultraviolet radiation to sanitize the object in the enclosed chamber in conjunction with the concentrated ozone.

18. The device of claim 1 wherein the enclosed chamber comprises a lid that can be opened to allow insertion of the object into the enclosed chamber; the lid, when closed, forms a seal that reduces ozone leakage from the enclosed chamber to acceptable levels; and the seal has a tongue and groove construction or uses a compliant sealing material.

19. The device of claim 1 wherein the enclosed chamber is configured to hold a mobile phone.

20. The device of claim 1 wherein the enclosed chamber comprises a floor with standoffs that support the object away from the floor, thereby allowing air flow between the object and the floor.

* * * * *